United States Patent
Jödecke et al.

(10) Patent No.: US 7,271,292 B2
(45) Date of Patent: Sep. 18, 2007

(54) PROCESS FOR DISTILLATIVELY REMOVING PIPERAZINE FROM AN ETHYLENEDIAMINE-PIPERAZINE MIXTURE

(75) Inventors: Michael Jödecke, Bobenheim-Roxheim (DE); Ortmund Lang, Quirnbach (DE); Gunther van Cauwenberge, Wachenheim (DE); Matthias Frauenkron, Kalmhout (NL)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/494,733

(22) Filed: Jul. 28, 2006

(65) Prior Publication Data

US 2007/0037980 A1    Feb. 15, 2007

(30) Foreign Application Priority Data

Aug. 13, 2005  (DE) ...................... 10 2005 038 376

(51) Int. Cl.
*C07C 209/84* (2006.01)
*C07C 209/86* (2006.01)
*C07D 295/023* (2006.01)

(52) U.S. Cl. ...................... 564/499; 564/497; 564/498; 544/358

(58) Field of Classification Search ...................... None
See application file for complete search history.

(56) References Cited

U.S. PATENT DOCUMENTS 3,105,019 A      9/1963  Murray, Jr. et al.
3,331,756 A *    7/1967  Currier et al. ................ 203/69
2007/0043217 A1* 2/2007  Siegert et al. .............. 544/358

FOREIGN PATENT DOCUMENTS

GB       1 263 588      2/1972

* cited by examiner

*Primary Examiner*—Brian Davis
(74) *Attorney, Agent, or Firm*—Oblon, Spivak, McClelland, Maier & Neustadt, P.C.

(57) ABSTRACT

The invention relates to a process for continuously, distillatively removing piperazine from an ethylenediamine-piperazine mixture under pressure at elevated temperature, by discharging the ethylenediamine at the top and the piperazine at the bottom of a distillation column. For the purpose of improving the quality of the piperazine, especially its color and color stability, the piperazine is subjected directly to circulation conveying it through an evaporator unit operated at a temperature of from about 160° C. to about 170° C. and returning it into the distillation column. After a residence time of from about 30 min to about 60 min in the circulation system, the piperazine is discharged in vapor form from a side draw in the lower section of the distillation column.

1 Claim, No Drawings

PROCESS FOR DISTILLATIVELY REMOVING PIPERAZINE FROM AN ETHYLENEDIAMINE-PIPERAZINE MIXTURE

The invention relates to a process for continuously, distillatively removing piperazine from an ethylenediamine-piperazine mixture under pressure at elevated temperature, by discharging the ethylenediamine at the top and the piperazine at the bottom of a distillation column.

Piperazine finds use in the preparation of pharmaceuticals for human and veterinary medicine, cosmetics and photographic chemicals. An important quality feature of piperazine, in addition to its purity (usually determined by gas chromatography), is the degree of discoloration and the color stability.

A measure employed for the degree of discoloration is usually the so-called color number. The color number is a characteristic value, determined under fixed conditions, for the color of transparent substances, which is usually determined by visual comparison. A frequently used color number in liquids is the APHA (American Public Health Association) color number (Römpp Chemie Lexikon 1995).

Piperazine is obtained in desired purity by known processes, by distillative removal of a product mixture. In this context, such high-performance distillation apparatus has become available that the ultimately obtained piperazine fraction already has the desired degree of purity. Thus, the distillation includes both the removal (isolation) process step and the purification step in one. From an economic point of view, this constitutes a particularly efficient method even if the piperazine first has to be fractionated repeatedly in one or more columns.

Piperazine is usually obtained on the industrial scale as one of the products of value in the preparation of various ethyleneamines. In this preparation, the synthesis is based on the reaction of ethylene dichloride (EDC process) or monoethanolamine (MEOA process) with ammonia. Further coproducts of this reaction are ethylenediamine (EDA), diethylenetriamine (DETA), triethylenetetramine (TETA) and higher linear and cyclic ethyleneamines, and also additionally aminoethylethanolamine (AEEA) in the MEOA process.

Both synthetic routes are based ultimately on the oxidation of ethylene (with chlorine or oxygen) to give EDC and ethylene oxide (EO) respectively, and subsequent one- or two-stage reaction with ammonia. Although the MEOA process thus includes an additional synthesis step, the chlorine oxidant is however expensive and formation of salt is additionally unavoidable.

In comparison to the EDC process, the MEOA process ensures an increased fraction of cyclic compounds, so that it constitutes the preferred process when a piperazine-containing product mix is desired.

Irrespective of the selection of the process, the ethyleneamine product mix in industrial production is purified and separated usually by means of a battery of columns in continuous operation. First, the ammonia is drawn off in a pressure column, then the process water formed (or added in the EDC process) is distilled off.

In this context, GB 1 263 588 describes the purification of the product mix by azeotropic removal of impurities in the distillative removal of water.

In contrast, U.S. Pat. No. 3,105,019 describes the addition of organic solvents as entraining agents for piperazine in the distillation, especially for the removal of a piperzine-TEDA fraction.

Although all of the above-described processes afford piperazine or other ethylamine products or product mixtures with sufficient purity, it is not guaranteed that the products will have sufficient color stability even when the color number determined corresponds to the requirements immediately after isolation.

This is because the discoloring components are generally not detectable as individual compounds and are, for example, below the detection limit in the gas chromatography purity check. Especially in the MEOA process, these compounds are based on acetaldehyde fractions and their condensed subsequent products. In this case, the chromophoric compounds are formed only in the course of time, so that a color number change often occurs only after storage to the effect that the desired specification is no longer attained.

These impurities appear especially in the MEOA process, since the amination of MEOA is based on ethylene units which enable the formation of C2 fragments by dehydration and deamination under the reaction conditions. These fragments, especially acetaldehyde and more highly condensed subsequent products, cause lasting deterioration in the product quality, especially in the color stability. However, it is also the case here that these impurities, owing to their inhomogeneity and low concentration, are generally analytically undetectable in the isolated components after distillation.

It was therefore an object of the invention to provide an improved, efficient and economically viable process for preparing pure piperazine with improved quality with regard to color, color stability and odor.

For the achievement of this object, the measures according to the characterizing part of the patent claim are proposed.

The invention uses an ethylenediamine-piperazine mixture which is obtained in a manner known per se. The mixture is separated in a distillation column under pressure and at elevated temperature. Suitable for this purpose is customary distillation apparatus with evaporator and condenser. Preference is given to using a distillation column having generally from 10 to 60, appropriately from 30 to 40 theoretical plates in the form of trays, structured packings or random packings. Useful trays include bubble-cap trays, sieve trays, valve trays, Thorman trays, Streuber trays or dual-flow trays. Preferred structured packings are compact sheetlike structures or fabrics of metal or plastic. Advantageous random packings are rings such as Raschig, Intos or Pall rings, saddles such as barrel or Intalox saddles, and also Top-Pak or braids.

The ethylenediamine-piperazine mixture is fed into the distillation column in the region of theoretical plates 5 to 20, in particular 10 to 15. The distillation is carried out in the pressure range from 0.5 to 2 bar, preferably from 0.8 to 1.5 bar, and at a temperature in the bottom of the column of from about 140 to about 170° C.

Owing to the thermal sensitivity of the ethylenediamine-piperazine mixture, it is appropriate to operate the distillation column with an evaporator which has a low wall temperature and a small liquid capacity. Overall, it has been found to be particularly advantageous to use a folding-film or thin-film evaporator. For gentle evaporation, a temperature difference between the vapor and the product side of $\leq 30°$ C., in particular $\leq 20°$ C. is recommended. The column bottom and the evaporator bottom are configured such that the residence time of the mixture is less than 60 minutes.

The ethylenediamine obtained by distillation is discharged at the top of the column and the piperazine at the bottom of the column. The ethylenediamine is fed as reflux back into the distillation column, this being adjusted such that the reflux ratio is from 0.4 to 0.8. According to the invention, the piperazine is subjected directly to a circulation conveying it through an evaporator unit operated at a temperature of from about 160° C. to about 170° C. and returning it into the distillation column. Suitable evaporator units are falling-film evaporators, thin-film evaporators, short-path evaporators or helical-tube evaporators. After a residence time of from 30 min to about 60 min in the circulation system, the piperazine is discharged continuously in vapor form from a side draw in the lower region of the distillation column.

The vaporous piperazine from the side draw can subsequently be condensed with a conventional condenser or with a piperazine quench with external cooler, and be obtained and stored in the form of chips or in another form.

The piperazine from the side draw has a high purity (piperazine content >99.9% by weight) and a low color number (<30 APHA). It also features improved color number stability. The piperazine which is drawn off in the bottom of the column likewise has a high purity. Since it is used for the preparation of the aqueous piperazine solution, the higher color number does not present any problem.

The improved color stability can be tested in a long-term test.

In the color number test, the color quality of a compound is determined generally by measuring the transmission of incident light. To this end, a light beam of defined wavelength is radiated through the melt or a solution of a certain concentration in a cuvette of known path length. The percentage of the light energy transmitted at a given wavelength gives rise to a defined color number. For weakly colored solutions, the APHA color scale is used.

The color number is measured in a spectrometer calibrated beforehand to the zero point with the water used in a 50 mm plastic cuvette. The piperazine is weighed into the cuvette in pulverized form, and care has to be taken that no excessive heating occurs as a result of friction. The entire operation also has to be carried out rapidly in a place with efficient air extraction, in order to minimize water ingress owing to the hygroscopicity of the piperazine.

The invention is illustrated in detail with reference to the examples which follow.

EXAMPLE 1

Comparative Example, Non Inventive

The experiments were carried out with a DN 50 bubble-cap tray column with 70 trays.

1500 g/h of a mixture of approx. 90% by weight of ethylenediamine and approx. 10% by weight piperazine were introduced. The feed was at tray 26. The reflux ratio was about 1:2. The column was operated at an absolute pressure of 1 bar, a top temperature of approx. 117° C. and a bottom temperature of approx. 150° C. The evaporation at the bottom of the column was effected with a circulation evaporator. The ethylenediamine was drawn off at the top of the column with high purity; the piperazine was drawn off at the bottom of the column. The piperazine thus obtained had a purity of at least 99.9% by weight, but had unsatisfactory properties with regard to its color, to its color number stability and to its odor and was therefore not saleable. Color numbers of 24 APHA immediately after the finishing and 65 APHA after 3 months were measured.

EXAMPLE 2

Inventive

The procedure of Example 1 was repeated except that the piperazine discharged at the bottom of the bubble-cap tray column was subjected to a circulation conveying through a falling-film evaporator operated at a temperature of 165° C. and returning it into the column. The residence time of the piperazine in the circulation system was about 40 min. This allowed the thermal stress on the piperazine in the bottom of the column to be reduced. Vaporous piperazine was then drawn off continuously via a side draw above the 4th tray of the bubble-cap tray column, condensed and finished. The ratio between the bottom draw and the side draw amount was approx. 1:1. Piperazine was obtained with a purity of >99.9% by weight. The color number and the color number stability were distinctly improved in comparison to the experiment according to Example 1. Color numbers of 16 APHA immediately after finishing and 42 APHA after 3 months were measured.

What is claimed is:

1. A process for continuously, distillatively removing piperazine from an ethylenediamine-piperazine mixture under pressure at elevated temperature, by discharging the ethylenediamine at the top and the piperazine at the bottom of a distillation column, which comprises subjecting the piperazine directly to a circulation conveying it through an evaporator unit operated at a temperature of from about 160° C. to about 170° C. and returning it into the distillation column, and, after a residence time of from 30 min to about 60 min in the circulation system, discharging it in vapor form from a side draw in the lower region of the distillation column.

* * * * *